United States Patent [19]

Berg

[11] Patent Number: 5,425,853
[45] Date of Patent: Jun. 20, 1995

[54] SEPARATION OF PROPYLENE GLYCOL FROM ETHYLENE GLYCOL BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 269,104

[22] Filed: Jun. 30, 1994

[51] Int. Cl.⁶ .......................... B01D 3/36; C07C 31/20
[52] U.S. Cl. ........................................ 203/57; 203/62; 203/68; 203/69; 203/70; 568/868
[58] Field of Search .................. 203/69, 68, 70, 57, 203/62; 568/868

[56] References Cited

U.S. PATENT DOCUMENTS

| | | | |
|---|---|---|---|
| 3,809,724 | 5/1974 | Golden | 203/70 |
| 4,935,102 | 6/1990 | Berg | 203/69 |
| 4,966,658 | 10/1990 | Berg | 203/69 |
| 4,980,033 | 12/1990 | Berg | 203/69 |

*Primary Examiner*—Wilbur Bascomb, Jr.

[57] ABSTRACT

Propylene glycol is difficult to separate from ethylene glycol by conventional distillation or rectification because of the proximity of their boiling points. Propylene glycol can be readily separated from ethlene glycol by azeotropic distillation. Effective agens are m-diisopropyl benzene, 1-octene, 3-carene and myrcene.

1 Claim, No Drawings

SEPARATION OF PROPYLENE GLYCOL FROM ETHYLENE GLYCOL BY AZEOTROPIC DISTILLATION

FIELD OF THE INVENTION

This invention relates to a method for separating propylene glycol from ethylene glycol using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical stage Requirements.

| Separation Purity, Both Products (Mole Fraction) | Relative volatility |  |  |  |  |  |  |  |
|---|---|---|---|---|---|---|---|---|
|  | 1.02 | 1.1 | 1.2 | 1.3 | 1.4 | 1.5 | 2.0 | 3.0 |
|  | Theoretical Stages at Total Reflux |  |  |  |  |  |  |  |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

There are a number of commercial processes which produce complex mixtures of glycols, e.g. the catalytic hydrocracking of sugars and starches. These processes usually produce a homologous series of glycols. Two of the commonest glycols usually present are propylene glycol and ethylene glycol. Propylene glycol boils at 187° C. and ethylene glycol boils at 198° C. The relative volatility between these two is 1.11 which makes it very difficult to separate them by conventional rectification. Azeotropic distillation would be an attractive method of effecting the separation of propylene glycol from ethylene glycol if agents can be found that (1) will create a large apparent relative volatility between propylene glycol and ethylene glycol and (2) are easy to recover from propylene glycol. Table 2 shows the relative volatility required to obtain 99% purity. With no agent, the relative volatility is 1.11 and 116 actual plates are required. With an agent giving a relative volatility of 1.8 only 22 plates are required.

TABLE 2

Theoretical and Actual Plates Required vs. Relative Volatility for Propylene Glycol - Ethylene Glycol Separation

| Relative Volatility | Theoretical Plates Required At Total Reflux, 99% Purity | Actual Plates Required 75% Efficiency |
|---|---|---|
| 1.11 | 97 | 116 |
| 1.5 | 23 | 31 |
| 1.8 | 16 | 22 |

TABLE 3

Effective Azeotropic Distillation Agents For Separating Propylene Glycol From Ethylene Glycol

| Compounds | Relative Volatility |
|---|---|
| None | 1.11 |
| Ethyl benzene | 1.25 |
| p-Xylene | 1.2 |
| n-Propyl benzene | 1.2 |
| o-Diethyl benzene | 1.3 |
| m-Diethyl benzene | 1.25 |
| m-Diisopropyl benzene | 1.7 |
| Cyclopentane | 1.8 |
| Methyl cyclohexane | 1.45 |
| 3-Methyl pentane | 1.25 |
| 2,3-Dimethyl butane | 1.2 |
| Heptane | 1.9 |
| 1-Heptene | 1.35 |
| Octane | 1.35 |
| 1-Octene | 1.9 |
| 2,3,4-Trimethyl pentane | 1.75 |
| Decane | 1.5 |
| Methyl ethyl ketoxime | 1.75 |
| Decalin | 1.21* |
| Dicylco pentadiene | 1.35 |
| alpha-Phellandrene | 1.35 |
| beta-Pinene | 1.30* |
| Myrcene | 1.29* |
| Terpinolene | 1.28* |
| p-Mentha-1,5-diene | 1.35 |
| 3-Carene | 1.8* |
| Limonene | 1.37* |
| alpha-Terninene | 1.35 |

*Data Obtained in Multiplate Rectification Column

OBJECTIVE OF THE INVENTION

The object of this invention is to provide a process or method of azeotropic distillation that will enhance the relative volatility of propylene glycol from ethylene glycol in their separation in a rectification column. It is a further object of this invention to identify organic compounds which in addition to the above constraints, are stable, can be separated from ethylene glycol and recyled to the azeotrope column with little decomposition.

SUMMARY OF THE INVENTION

The objects of this invention are to provide a process for separating propylene glycol from ethylene glycol which entails the use of certain organic compounds as the agent in azeotropic distillation.

DETAILED DESCRIPTION OF THE INVENTION

I have discovered that certain organic compounds will greatly improve the relative volatility of propylene glycol to ethylene glycol and permit the separation of propylene glycol from ethylene glycol by rectification when employed as the agent in azeotropic distillation. Table 3 lists the compounds that I have found to be effective. They are ethyl benzene, p-xylene, n-propyl benzene, o-diethyl benzene, m-diethyl benzene, m-diisopropyl benzene, cyclopentane, methyl cyclohexane, 3-methyl pentane, 2,3-dimethyl butane, heptane, 1-heptene, octane, 1-octene, 2,3,4-trimethyl pentane, decane, methyl ethyl ketoxime, decalin, dicyclo pentadiene, alpha-phellandrene, beta-pinene, myrcene, terpinolene, p-mentha-1,5-diene, 3-carene, limonene and alpha-terpinene.

THE USEFULNESS OF THE INVENTION

The usefulness or utility of this invention can be demonstrated by referring to the data presented in Tables 2 and 3. All of the successful agents show that propylene glycol can be separated from ethylene glycol by means of azeotropic distillation in a rectification column and that the ease of separation as measured by relative volatility is considerable.

WORKING EXAMPLES

Example 1

Twenty-seven grams of propylene glycol, 13 grams of ethylene glycol and 40 grams of 1-octene were charged to a vapor-liquid equilibrium still and refluxed for 13 hours. Analysis indicated a vapor composition of 79.1% propylene glycol, 20.9% ethylene glycol; a liquid compostion of 66.2% propylene glycol, 33.8% ethylene glycol. This is a relative volatility of 1.9.

Example 2

One hundred grams of a mixture comprising 75% propylene glycol and 25% ethylene glycol and 150 grams of myrcene were placed in the stillpot of a 5.6 theoretical plate glass perforated plate rectification column and refluxed for three hours. The overhead composition was 84.7% propylene glycol and 15.3% ethylene glycol; the bottoms composition was 56.8% propylene glycol, 43.2% ethylene glycol. This is a relative volatility of 1.29.

Example 3

Seventy grams of propylene glycol, 30 grams of ethylene glycol and 140 grams of 3-carene were placed in the stillpot of a 5.6 theoretical plate glass perforated plate rectification column and refluxed for four hours. The overhead composition was 84.1% propylene glycol and 15.9% ethylene glycol; the bottoms composition was 16.8% propylene glycol and 83.2% ethylene glycol. This is a relative volatility of 1.8.

I claim:

1. A method for recovering propylene glycol from a mixture of propylene glycol and ethylene glycol which comprises distilling a mixture of propylene glycol and ethylene glycol in the presence of an azeotrope forming agent, recovering the propylene glycol and the azeotrope forming agent as overhead product and obtaining the ethylene glycol as bottoms product, wherein said azeotrope forming agent consists of one material selected from the group consisting of ethyl benzene, p-xylene, n-propyl benzene, o-diethyl benzene, m-diethyl benzene, m-diisopropyl benzene, cyclopentane, methyl cyclohexane, 3-methyl pentane, 2,3-dimethyl butane, heptane, 1-heptene, octane, 1-octene, 2,3,4-trimethyl pentane, decane, methyl ethyl ketoxime, decalin, dicyclo pentadiene, alpha-phellandrene, beta-pinene, myrcene, terpinolene, p-mentha-1,5-diene, 3-carene, limonene and alpha-terpinene.

* * * * *